US00PP34829P3

(12) United States Plant Patent
Richmond

(10) Patent No.: US PP34,829 P3
(45) Date of Patent: Dec. 13, 2022

(54) ***CANNABIS* PLANT NAMED BAGZXCD6-PA#2**

(50) Latin Name: *Cannabis sativa*
Varietal Denomination: 'BAGZXCD6-PA#2'

(71) Applicant: BioAgronomics Group, Thousand Oaks, CA (US)

(72) Inventor: Mojave Richmond, Thousand Oaks, CA (US)

(73) Assignee: BioAgronomics Group, Thousand Oaks, CA (US)

( * ) Notice: Subject to any disclaimer, the term of this patent is extended or adjusted under 35 U.S.C. 154(b) by 0 days.

(21) Appl. No.: 17/803,042

(22) Filed: Jan. 24, 2022

(65) Prior Publication Data

US 2022/0240425 P1 Jul. 28, 2022

Related U.S. Application Data

(60) Provisional application No. 63/141,418, filed on Jan. 25, 2021.

(51) Int. Cl.
*A01H 5/12* (2018.01)
*A01H 5/02* (2018.01)
*A01H 6/28* (2018.01)

(52) U.S. Cl.
USPC ..... Plt./258
CPC ..... *A01H 6/28* (2018.05)

(58) Field of Classification Search
USPC ..... Plt./258
CPC ..... A01H 6/28; A01H 5/02; A01H 5/12
See application file for complete search history.

*Primary Examiner* — Keith O. Robinson
(74) *Attorney, Agent, or Firm* — Plant & Planet Law Firm

(57) ABSTRACT

The unique annual herbaceous *Cannabis* plant variety 'BAGZXCD6-PA #2' is provided. 'BAGZXCD6-PA #2' is a terpinolene-dominant variety with a shorter 9-week flowering period.

6 Drawing Sheets

Latin name of the genus and species:
Genus—*Cannabis.*
Species—*sativa.*
Variety denomination: The new *Cannabis* plant claimed is of the variety denominated 'BAGZXCD6-PA #2'.

BACKGROUND OF THE INVENTION

Field of the Invention

The present invention relates to a new and distinct annual variety of *C. sativa*, which has been given the variety denomination of 'BAGZXCD6-PA #2'. 'BAGZXCD6-PA #2' is intended for use as a medicinal herb for sale in *Cannabis* dispensaries; as source material for high value cannabinoid extraction; and to make products containing THC, CBG, and various aromatic compounds. This variety also has value as part of a breeding program to develop improved *Cannabis* varieties.

Background of the Related Art

The genus *Cannabis* has been in use by humans for millennia, due to the multiplicity of its benefits to humans, including the considerable value and utility of its fiber, the nutritional value of its seeds, and the medicinal value of its floral parts and products made from them. Currently the genus is under intense legal commercialization in the United States as industrial hemp for a variety of purposes including biodegradable plastics and building materials, clothing, paper, food, fuel, and medicines.

Cannabidiol (CBD) extracted from *Cannabis* is widely used in over-the-counter medicines and topical treatments and is also the active ingredient in the FDA-approved drug Epidiolex®, a prescription cannabidiol (CBD). CBD is just one of at least dozens—perhaps hundreds—of cannabinoids endogenous to *Cannabis*, tetrahydrocannabinol (THC) being the other cannabinoid that is most well-known. The cannabinoids as a group interact with the human endocannabinoid receptors, which are distributed in the brain and throughout the body. The study of the endocannabinoid system (ECS) in humans and other mammals is an area of increasing interest and holds tremendous promise for the future of medicine. See, e.g., Russo (2019) *Cannabis* and Pain, *Pain Medicine,* 1;20(11):2083-2085; and Russo (2016) Clinical Endocannabinoid Deficiency Reconsidered: Current Research Supports the Theory in Migraine, Fibromyalgia, Irritable Bowel, and Other Treatment-Resistant Syndromes, *Cannabis Cannabinoid Res.* 1(1): 154-165.

Typically, marijuana products are available to users for purchase in specialized "dispensaries" that offer dried flower, edibles, tinctures, extracts, and the like. In some cases, a unique or unusual chemical profile, or chemotype, is attractive not only for flower sales but also for use in the preparation of extracts and/or isolates and for the manufacture of a variety of products that possess characteristics of the chemotype.

SUMMARY OF THE INVENTION

The present invention relates to a new and distinct annual variety of *C. sativa*, which has been given the variety denomination of 'BAGZXCD6-PA #2'. 'BAGZXCD6-PA #2' is intended for use as a medicinal herb for sale in *Cannabis* dispensaries; as source material for high value cannabinoid extraction; and to make products containing THC, CBG, and various aromatic compounds. This variety also has value as part of a breeding program to develop improved *Cannabis* varieties.

The new *C. sativa* variety is a selection resulting from a sexual cross of *C. sativa* plants in Los Angeles, Calif., involving a seed parent known as 'ZETA' (unpatented) and a pollen parent known as 'ChemD' (unpatented). FIG. 6 depicts the lineage of the new variety.

Selection criteria were earlier maturation, high terpinolene content, and pest/pathogen resistance. Flower samples were grown indoors under High Pressure Sodium lamps in 3-gallon containers filled with 70% coco coir and 30% perlite. Using drip emitters, plants were fed a nutrient solution with an Electrical Conductivity (EC) between 0.8 and 2.5 and a pH between 5.8 and 6.2.

The selection was subsequently evaluated for a number of years in Los Angeles, Calif.

Asexual reproduction of the new variety by cutting propagation in a greenhouse since 2017 in Los Angeles, Calif. has demonstrated that the new variety reproduces true to type with all of the characteristics, as herein described, firmly fixed and retained through successive generations of such asexual propagation. A stable seed line of the new variety has also been developed by successive generations of inter-breeding and selection in order to correspond to the phenotypic characteristics described herein.

'BAGZXCD6-PA #2' is a terpinolene-dominant variety with a shorter 9-week flowering period. The inflorescence has longer stigmas that grow particularly straight. The stigmas are longer compared to both parents and longer than many varieties such as 'Hindu Kush' (unpatented) and 'Super Skunk' (unpatented). The trichome heads separate easily from the stalk making this variety more efficient for mechanical extraction.

Table 1 provides a genotype analysis of 'BAGZXCD6-PA #2' showing the closest genetic relatives:

TABLE 1

Genotype Analysis:

| % Contribution | Variety/Strain |
|---|---|
| 14.0625% | 'Haze' (unpatented) |
| 14.0625% | 'Afghani' (unpatented) |
| 4.6875% | 'Chamba' (unpatented) |
| 4.6875% | 'Rock Hard Indica' (unpatented) |
| 12.5% | 'OG Kush' (unpatented) |
| 25% | 'Chem Dog' (unpatented) |
| 25% | 'Sour Diesel' (unpatented) |

The tables below show an analysis of key cannabinoids and terpenes in this variety.

TABLE 2

Exemplary Profile of Key Cannabinoids.

| Cannabinoid | mg/g | % | LOD/LOQ mg/g |
|---|---|---|---|
| Δ9THC | 15.968 | 1.5968 | 0.052/0.158 |
| THCa | 282.596 | 28.2596 | 0.052/0.156 |
| THCVa | 3.003 | 0.3003 | 0.088/0.267 |
| CBDa | 0.998 | 0.0998 | 0.052/0.156 |
| CBG | 1.036 | 0.1036 | 0.048/0.144 |
| CBGa | 19.977 | 1.9977 | 0.034/0.102 |
| CBC | 0.166 | 0.0166 | 0.048/0.146 |
| CBCa | 2.713 | 0.2713 | 0.233/0.705 |
| Sum of Cannabinoids | 326.457 | 32.6457 | |
| Total THC (Δ9THC + 0.877 * THCa) | 263.805 | 26.3805 | |

TABLE 2-continued

Exemplary Profile of Key Cannabinoids.

| Cannabinoid | mg/g | % | LOD/LOQ mg/g |
|---|---|---|---|
| Total CBD (CBD + 0.877 * CBDa) | 0.875 | 0.0875 | |

TABLE 2

Exemplary Profile of Key Terpenes.

| Terpene | mg/g | % | LOD/LOQ mg/g |
|---|---|---|---|
| Camphene | <LOQ | <LOQ | 0.038/0.116 |
| Sabinene | 0.087 | 0.0087 | 0.024/0.073 |
| Myrcene | 7.032 | 0.7032 | 0.03/0.092 |
| α Phellandrene | 0.497 | 0.0497 | 0.048/0.144 |
| 3 Carene | 0.482 | 0.0482 | 0.028/0.085 |
| Limonene | 2.98 | 0.2980 | 0.04/0.12 |
| Ocimene | 1.64 | 0.1640 | 0.053/0.16 |
| Sabinene Hydrate | <LOQ | <LOQ | 0.046/0.138 |
| Terpinolene | 15.763 | 1.5763 | 0.042/0.128 |
| Linalool | 0.66 | 0.0660 | 0.043/0.13 |
| Fenchol | 0.256 | 0.0256 | 0.051/0.153 |
| Borneol | <LOQ | <LOQ | 0.063/0.19 |
| Terpineol | 0.430 | 0.0430 | 0.029/0.087 |
| β Caryophyllene | 2.056 | 0.2056 | 0.029/0.087 |
| α Humulene | 0.587 | 0.0587 | 0.017/0.051 |
| Valencene | <LOQ | <LOQ | 0.018/0.055 |
| Caryophyllene Oxide | 0.418 | 0.0418 | 0.011/0.034 |
| α Bisabolol | 0.311 | 0.0311 | 0.057/0.172 |
| Total Terpene Concentration | 35.651 | 3.5651 | |

Plants of the new variety differ from plants of the seed parent 'ZETA' primarily in morphology and chemotype. The new variety has longer stigmas as well as lower bract to leaf ratio then 'ZETA'. The new variety has higher amounts of the terpenoids myrcene, limonene, and caryophyllene than 'ZETA'. The new variety has higher levels of THCA and CB GA than 'ZETA'.

BRIEF DESCRIPTION OF THE DRAWINGS

The accompanying photographic illustrations show the typical appearance of the new variety 'BAGZXCD6-PA #2'. The colors are as nearly true as is reasonably possible in a color representation of this type. Colors in the photographs may differ slightly from the color values cited in the detailed botanical description, which accurately describes the colors of the new plant.

DETAILED BOTANICAL DESCRIPTION

Figure 1:
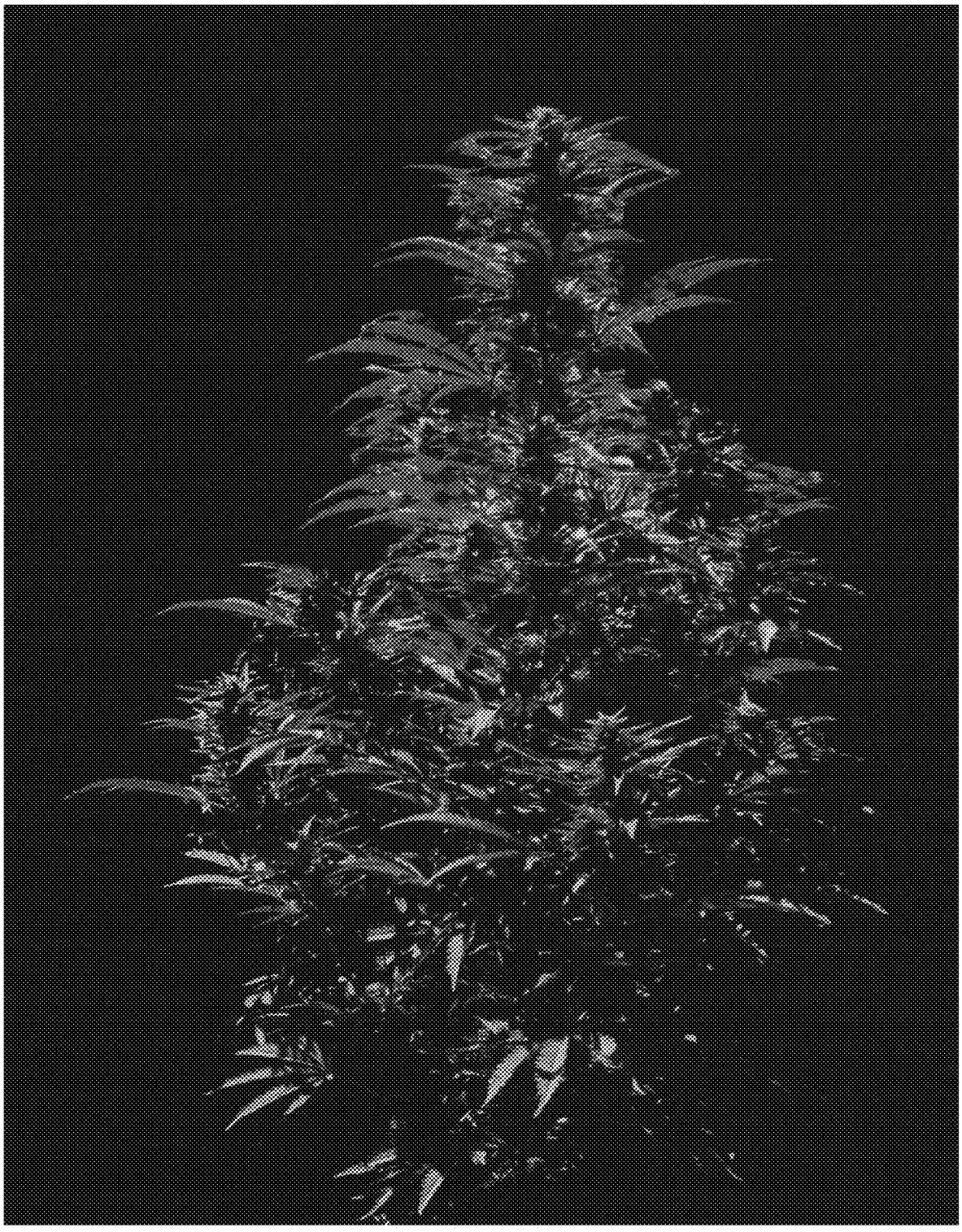
FIG. 1 is a photograph of the whole plant of the new variety 'BAGZXCD6-PA #2' grown outdoors at 60 days after inducing flowering.
Figure 2:
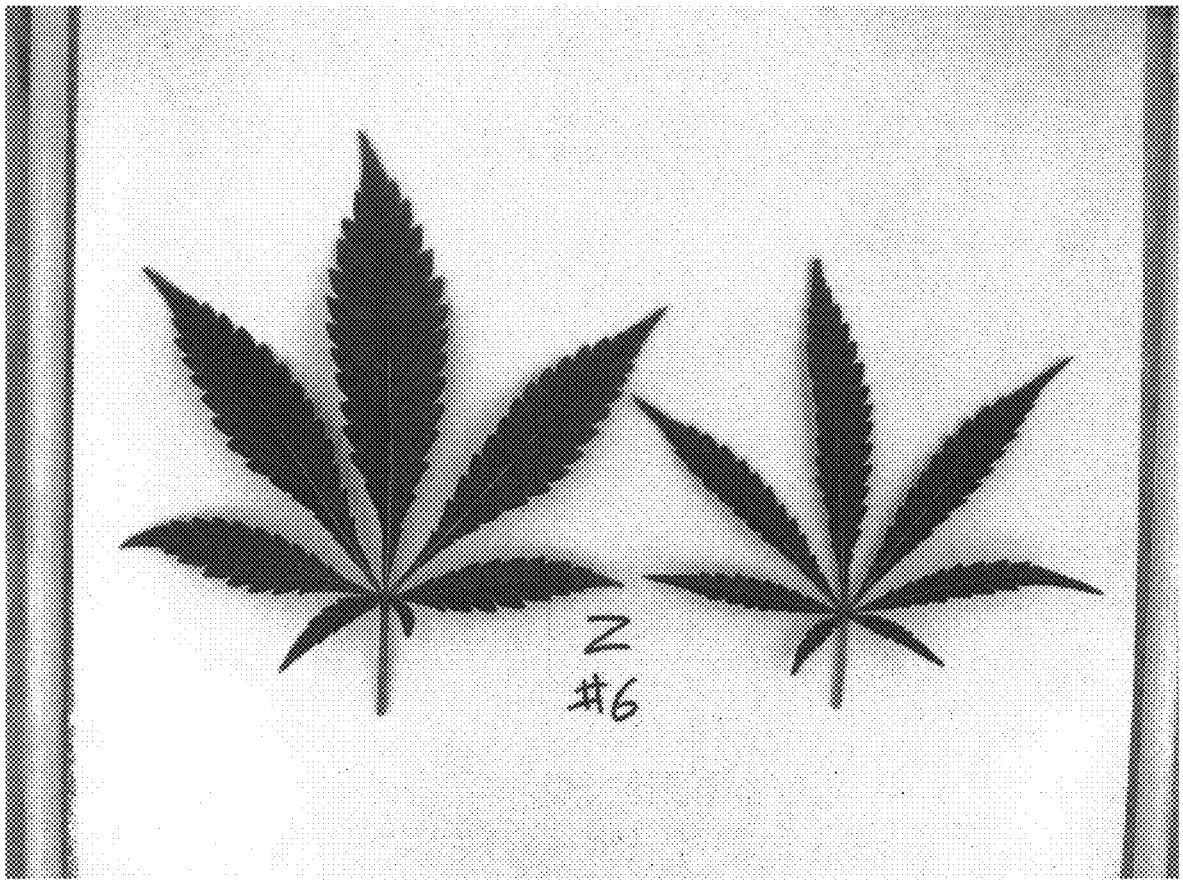
FIG. 2 is a photograph of 2 leaves of the new variety 'BAGZXCD6-PA #2' at 67 days after inducing flowering.
Figure 3:
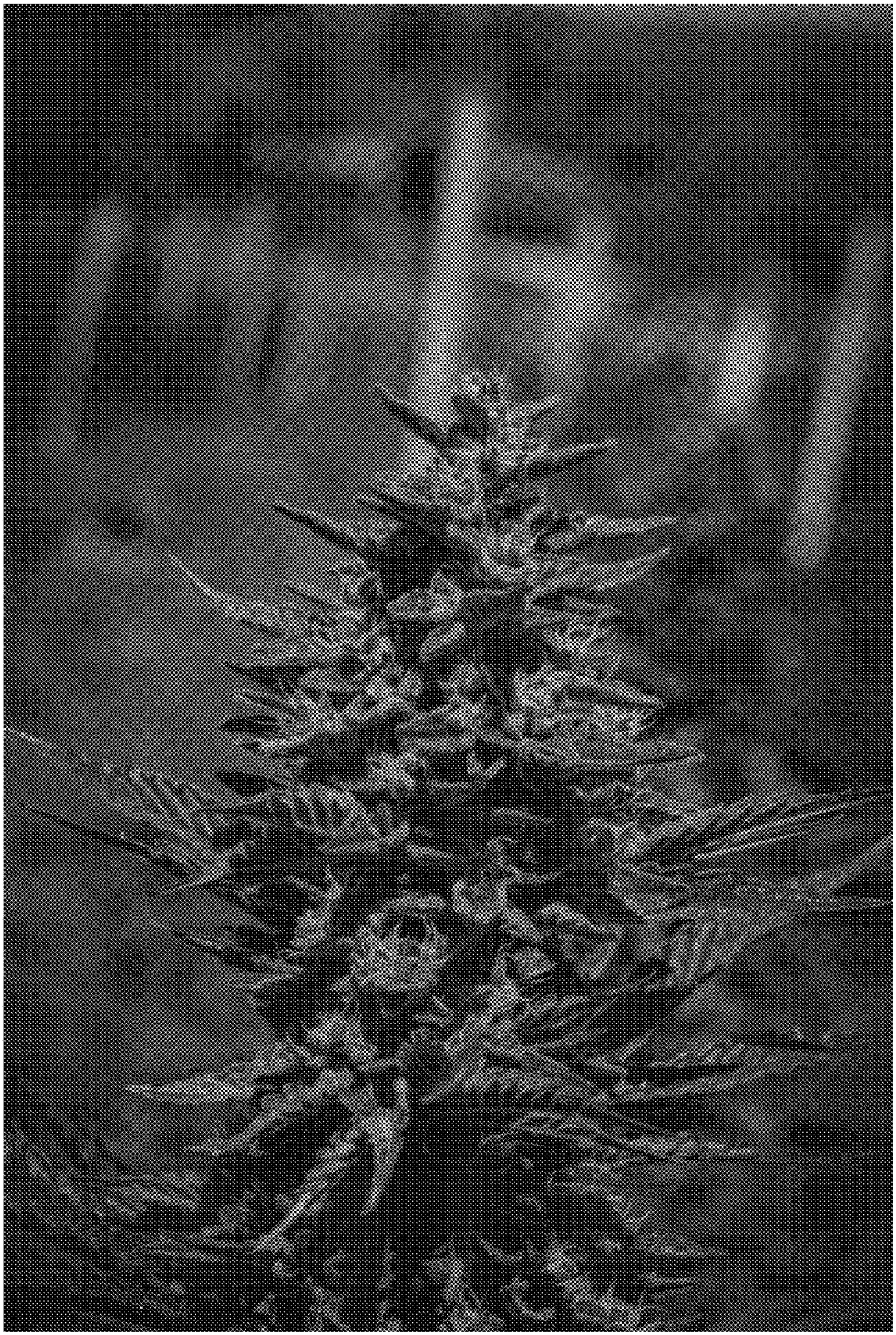
FIG. 3 is a photograph of a flower of the new variety 'BAGZXCD6-PA #2' grown outdoors at 60 days after inducing flowering.
Figure 4:
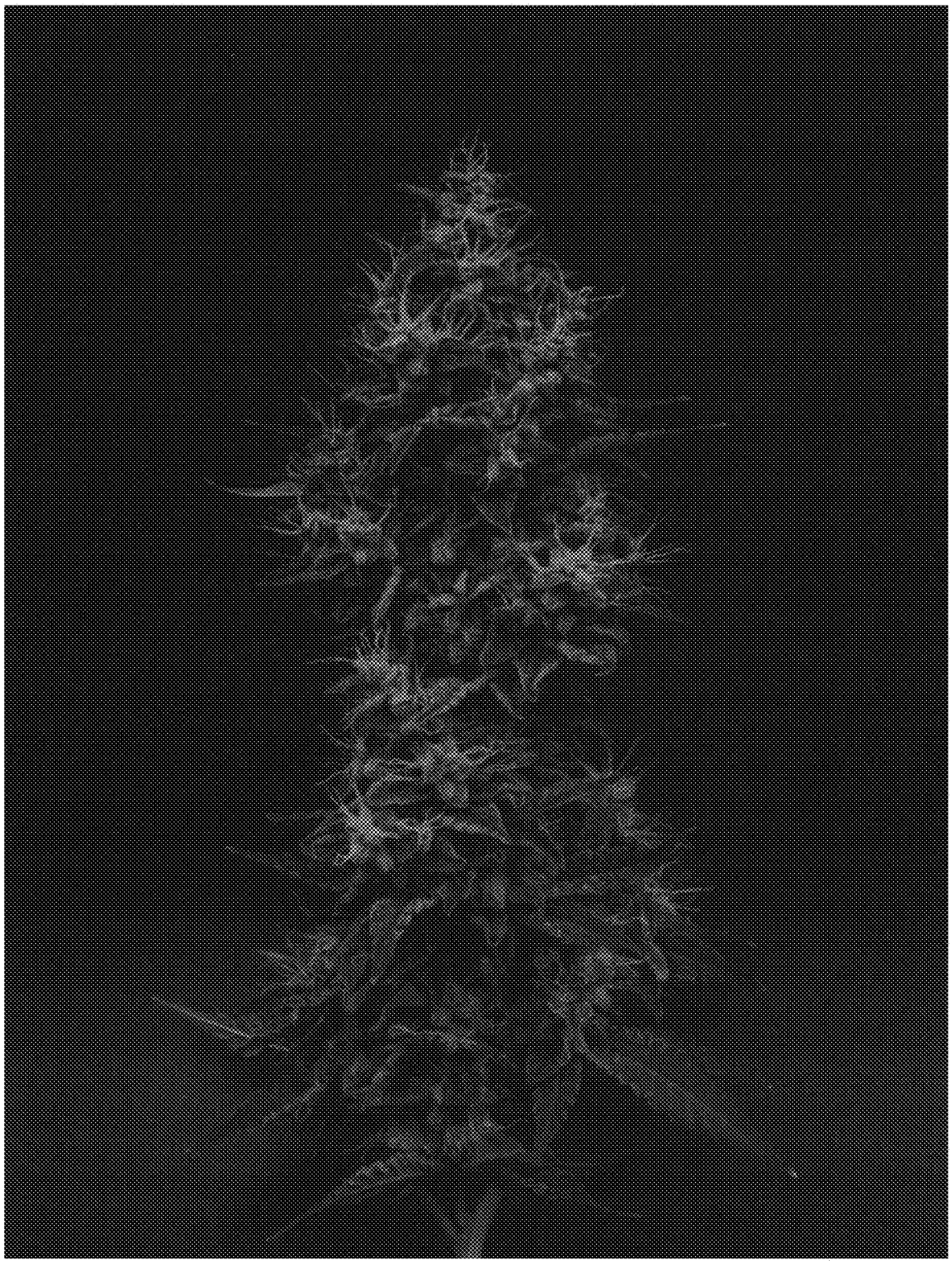
FIG. 4 is a photograph of a harvested flower of the new variety 'BAGZXCD6-PA #2' gown indoors under artificial lighting at 67 days after inducing flowering.
Figure 5:
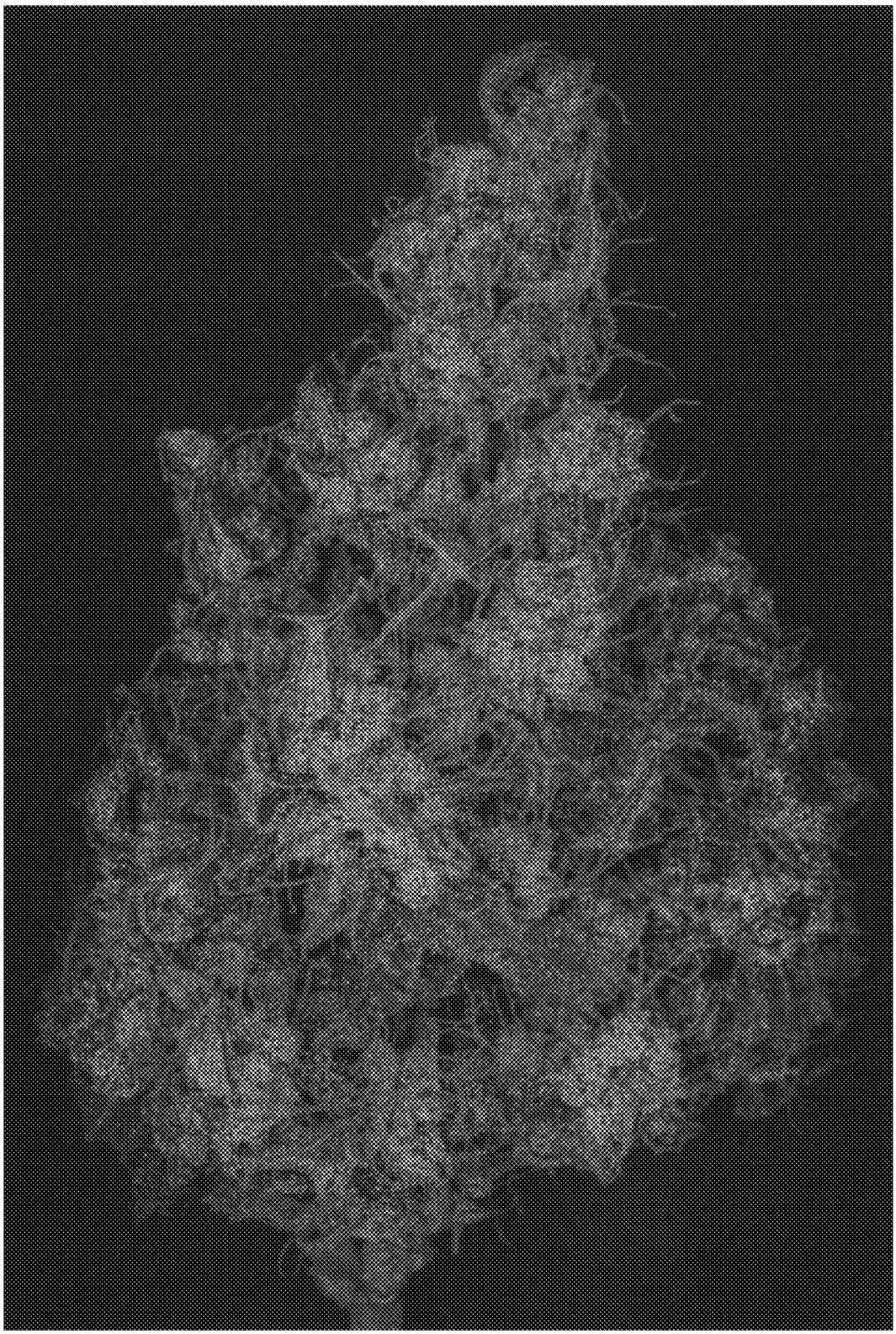
FIG. 5 is a photograph of a dry flower of the new variety 'BAGZXCD6-PA #2' grown indoors under artificial lighting.
Figure 6:
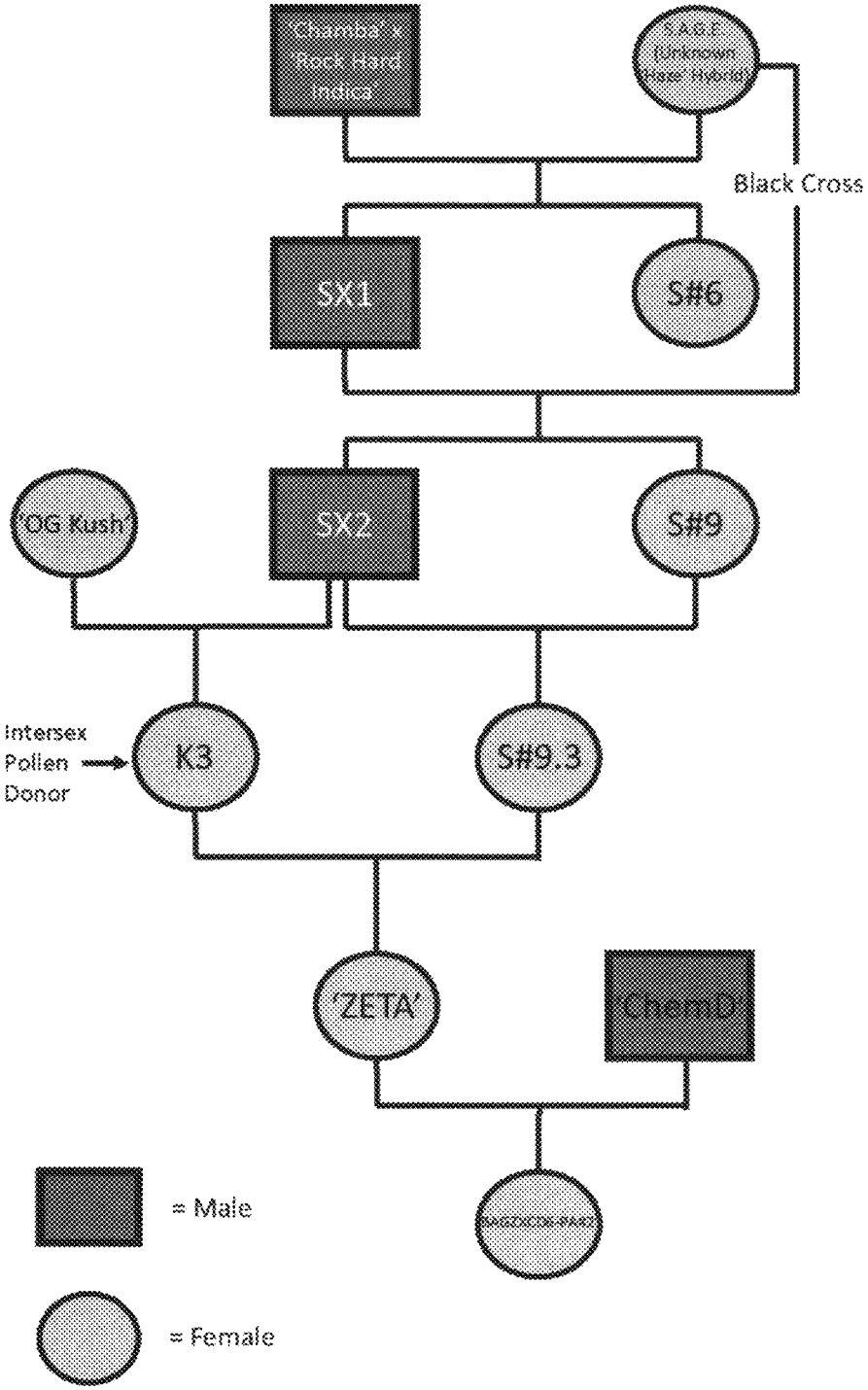
FIG. 6 is a depiction of the lineage of the new variety 'BAGZXCD6-PA #2'.

The following detailed description sets forth the distinctive characteristics of 'BAGZXCD6-PA #2'. The data which defines these characteristics was collected from asexual reproductions of the original selection at age 60 days old (after cutting rooted). Dimensions, sizes, colors, and other characteristics are approximations and averages set forth as accurately as possible. The descriptions relate to plants grown in Los Angeles, Calif. Color notations are from "RAL K1 Classic" 2018.

Type: Herbaceous annual.

Classification:

a. *Family*.—Cannabaceae.
b. *Genus*.—*Cannabis*.
c. *Species*.—*Sativa*.
d. *Common name*.—Marijuana.

PLANT

General:

a. *Origin*.—Traditional landraces.
b. *Parentage*.—i. Female parent — 'ZETA'. ii. Male parent — 'ChemD'.
c. *Growth habit*.—Herbaceous, erect, and well-branched.
d. *Average height*.—Variable based on agronomic conditions (4 to 10 feet).
e. *Average spread*.—Variable based on agronomic conditions (2 to 6 feet).
f. *Growth rate*.—Vigorous rapid growth.
g. *Flower storage life*.—6 months or longer when refrigerated.
h. *Productivity*.—40-90 grams/square foot.
i. *Disease resistance*.—Powdery mildew (*Golovinomyces* spp.) and Gray mold (*Botrytis cinerea*).
j. *Pest resistance*.—Two-spot spider mite (*Tetranycus urticae*).
k. *Fragrance*.—Spicy, herbal, fruity, earthy, and fuel.
l. *Type of inflorescence*.—Cymose.
m. *Photoperiodicity*.—Short-day/Long-night.
n. *Number of flowers per cyme*.—10-500.
o. *Pollen description*.—None. This is a vegetatively propagated female plant.
p. *Hardiness*.—Outdoors in California late spring through early autumn USDA Hardiness Zone 6 and higher; Indoors 65-75° F. (18-24° C.).

STEM/CENTRAL STALK

General:

a. *Average diameter*.—1 to 6 inches at the soil level.
b. *Shape*.—Roughly cylindrical.
c. *Average length of internode*.—3 to 10 inches.
d. *Depth of grooves*.—Shallow.
e. *Pith in cross section*.—Thin.
f. *Trichome type*.—Predominately capitate stalked.
g. *Color*.—Light green Medium green (575C Pantone PMS).
h. *Average length*.—4 to 10 feet.

LEAF

General:

a. *Quantity*.—Leaf size diminishes as inflorescences develop.
b. *Leaf color* (*top side*).—Medium green (2266C Pantone PMS).
c. *Leaf color* (*under side*).—Lighter green (P162-8U Pantone PMS).
d. *Leaf arrangement*.—Alternate.
e. *Leaf shape*.—Compound pinnate.
f. *Leaf margins*.—Serrated.
g. *Undulation of margin*.—Slight.
h. *Leaflet apex shape*.—Multiple distally pointed leaflets in each compound pinnate leaf.
i. *Leaflet base shape*.—Multiple basally narrowed leaflets in each compound pinnate leaf.
j. *Average leaf width*.—5 to 10 inches.
k. *Average leaf length*.—5 to 10 inches.
l. *Number of leaflets per leaf*.—5 to seven.
m. *Central leaflet length*.—5 to 10 inches.
n. *Central leaflet width*.—1 to 2.5 inches.
o. *Number of serrations in the middle leaflet*.—12 to 16.
p. *Margin type*.—Serrated.
q. *Trichome type* (*top surface*).—Few cystolithic.
r. *Trichome type* (*bottom surface*).—Cystolithic with few bulbous.
s. *Texture of top and bottom surfaces*.—Smoother on the adaxial surface; more trichomes on abaxial surface.
t. *Appearance of top and bottom surfaces*.—Medium green (2266C Pantone PMS) on adaxial surface; lighter green (P162-8U Pantone PMS) on the abaxial surface.
u. *Venation type*.—Compound pinnate.

PETIOLE

General:

a. *Length*.—30 to 40 percent of central leaflet length. The average length is 0.5-2.5 inches.
b. *Surface texture*.—Slightly rough.
c. *Anthocyanin intensity*.—Occasional anthocyanin pigmentations.
d. *Color*.—Light green (P159-13C Pantone PMS) with occasional red (P60-10C Pantone PMS).
e. *Diameter*.—1/16-1/8 inch (1.5-3.0 millimeters).
f. *Strength*.—Strong.

FEMALE FLOWER

General:

a. *Natural flowering season*.—Summer through early Autumn.
b. *Average size*.—1/8 inch (3 millimeters) in length.
c. *Quantity per inflorescence*.—10-500 or more per cyme.
d. *Description when flower has bracts with no styles*.—Emerging small bracts.
e. *Description when flower has styles on the first flowers*.—Bracts beginning to enlarge.
f. *Description when 50% of the bracts are formed*.—Bracts reaching full size.

g. *General description of stigma*.—Cream white (7767U Pantone PMS) to red brown (7510U Pantone PMS).

h. *General description of bract*.—Surrounds the unfertilized ovule. Covered with capitate- stalked trichomes.

i. *General description of terminal inflorescence*.—Compact cyme consisting of many bracts with subtending leaflets.

j. *General description of node*.—Prominent with paired stipules.

k. *Average diameter*.—1/16 inch (1.5 millimeters).

l. *Color*.—2266C Pantone PMS.

m. *Petals per flower*.—None.

n. *Bract*.—i. Size — 1/8 inch or 3 millimeters in length. ii. Quantity — 10-500 or more per cyme. iii. Shape — Vase-shaped with rounded base and elongated tip. iv. Trichome type — Predominately capitate-stalked. v. Color — light green (P162-8U Pantone PMS) to medium green (2266C Pantone PMS). vi. Texture — Sticky as a result of predominate capitate-stalked resin gland exudate.

o. *Bracteole*.—Highly reduced or absent.

p. *Stigma*.—i. Size — Average 13/64 inch (5 millimeters) in length. ii. Quantity — One pair per ovule within a single bract. iii. Shape — Long and pointed and feathery. iv. Trichome type — None. v. Color — Cream white (7767U Pantone PMS) to red brown (7510U Pantone PMS).

q. *Stipule*.—i. Size — 3/64 inch or 1 millimeter in length. ii. Quantity — One pair at each node. iii. Shape — Narrow pointed triangle. iv. Trichome type — Cystolithic. v. Color — Light green (P162-8U Pantone PMS).

r. *Ovary*.—i. Position — Enveloped by bract. ii. Shape — Tiny undeveloped. iii. Length — Miniscule. iv. Color — Cream white (7767U Pantone PMS).

s. *Pedicel*.—None. Note: Bracts are sessile and without a pedicel.

t. *Pistil*.—Note: Fused stigma and style form the pistil. i. Length — Average 13/64 inch (5 millimeters) in length. ii. Number per flower — One.

u. *Style*.—i. Length — Average 13/64 inch (5 millimeters) in length. ii. Color — Cream white (7767U Pantone PMS) to red brown (7510U Pantone PMS).

The invention claimed is:

1. A new and distinct variety of *Cannabis* plant named 'BAGZXCD6-PA #2', as illustrated and described herein.

* * * * *